United States Patent [19]

Kutscher et al.

[11] Patent Number: 5,770,574
[45] Date of Patent: Jun. 23, 1998

[54] LONG-CHAIN ALKYLAMIDES OF AMINO ACIDS AND PEPTIDES WITH ANTI-PROLIFERATIVE AND ANTI-INFLAMMATORY PROPERTIES

[75] Inventors: Bernhard Kutscher, Maintal; Michael Bernd, Frankfurt; Heinz Grossmann, Regensburg; Maria Kick, Regensburg; Jürgen Arp, Regensburg; Manfred Liefländer, Sinzing; Jürgen Engel, Alzenau; Rainer Voegeli, Offenbach, all of Germany

[73] Assignee: ASTA Medica Aktiengesellschaft, Dresden, Germany

[21] Appl. No.: 878,842

[22] Filed: Jun. 19, 1997

Related U.S. Application Data

[63] Continuation of Ser. No. 399,711, Mar. 3, 1995, abandoned.

[30] Foreign Application Priority Data

Mar. 4, 1994 [DE] Germany .......................... 44 07 193.0

[51] Int. Cl.$^6$ .......................... A61K 38/05; A61K 38/06; C07K 5/00
[52] U.S. Cl. .............................. 514/18; 514/19; 530/330; 530/331; 548/535; 562/562; 562/567
[58] Field of Search ........................ 514/18, 19; 530/320, 530/331; 548/535; 562/562, 567

[56] References Cited

FOREIGN PATENT DOCUMENTS 490338    4/1967   Switzerland .

OTHER PUBLICATIONS

Chemical Abstract 96:20447m, Reig et al., "Synthesis of a new family of surface active agents The enkephalin alkyl amides", vol. 96, (1982) p. 491.

Chemical Abstract 115:280524s, Kellner et al., "Synthesis and properties of lipo amino acids and lipodipeptides of ornithine", vol. 115 (1991) pp. 1066–1067.

*Primary Examiner*—Cecilia J. Tsang
*Assistant Examiner*—Bennett Celsa
*Attorney, Agent, or Firm*—Cushman, Darby & Cushman IP Group of Pillsbury Madison & Sutro LLP

[57]   ABSTRACT

Long-chain, unbranched alkylamides of the general formula $$CH_3-(CH_2)_nN-NH-R$$

in which n=11–20 and R=amino acid, its D- and L-enantiomers, di- and tripeptides, forms derived by N-protective groups, and terminal ethyl esters as well as its physiologically compatible salt forms as active pharmaceutical substances with anti-proliferative and anti-inflammatory properties.

8 Claims, No Drawings

LONG-CHAIN ALKYLAMIDES OF AMINO ACIDS AND PEPTIDES WITH ANTI-PROLIFERATIVE AND ANTI-INFLAMMATORY PROPERTIES

This is a continuation of application Ser. No. 08/399,711, filed on Mar. 3, 1995 (abandoned).

The invention is related to novel lipoamino acids, lipodipeptides and lipotripeptides, their production and use as active pharmaceutical substances.

BACKGROUND OF THE INVENTION

The derivatives according to the general formula

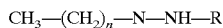

in which n=11–20 and R=amino acid, its D- and L-enantiomers, di- and tripeptides, forms derived by N-protective groups, and terminal ethyl esters as well as its physiologically compatible salt forms are suitable as active pharmaceutical substances to influence and suppress tumor growth in vitro and in vivo as well as to inhibit protein kinase C.

They are furthermore suitable for intervening in the arachidonic-acid metabolism and of being pharmacologically active in tissue-inflammatory processes by means of phospholipase $A_2$ inhibition. The derivatives cited are capable of inhibiting lipoxygenase and cyclooxygenase in low micromolecular ($\mu$m) concentration, during which nonspecific release of histamine is not observed. Lipoxygenase, cyclooxygenase and phospholipase $A_2$ produce catabolites of the arachidonic-acid cascade from phospholipids; such arachidonic-acid metabolites are inflammatorily active and participate to a considerable extent in the pathogenesis and maintenance of pathophysiologic processes such as bronchial asthma, hay fever [allergic rhinitis], muscular rheumatism and others. Amino acids and short-chain peptides from neutral and/or basic amino acids with long aliphatic groups frequently exhibit amphiphilic properties. Amphiphilic substances are distinguished by the simultaneous presence of hydrophilic and hydrophobic molecular areas. They therefore exhibit a structural relationship with membrane elements. Lipoamino acids with the formula H-Orn-NHR.2HBr (R=$C_{16}H_{33}$, $C_{18}H_{37}$) and lipodipeptides with the formula H-Orn-Orn-NHC$_{18}$H$_{37}$.3HCl and their preparation are described by G. Kellner and M. Lieflander in Z. Naturforsch. B., Chem. Sci. 46(8) 1098–1104 (1991). However, the use of these compounds as active pharmaceutical substances with anti-proliferative and anti-inflammatory properties is not known. Swiss patent 490,338 (Chem. Abstr. vol. 73 120 904 b (1970)) cites the preparation of Z-L-Lys(BOC)-L-Lys(BOC)-L-Pro-NH-n-C$_{16}$H$_{33}$. However, an appropriate pharmaceutical use is not indicated. PCT application WO 8806885 describes, among other things, the preparation of H-D-Pro-NH-C$_{16}$H$_{33}$ and its use as phospholipase $A_2$ inhibitor. However, no suggestion about an anti-proliferative property and an inhibitory action on the growth of primary tumors of this or of related compounds is indicated.

SUMMARY OF THE INVENTION

This action is shown in tests with compounds of the general formula

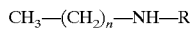

in which n=11–20 and R=amino acid, its D- and L-enantiomers, di- and tripeptides, forms derived by N-protective groups, and terminal ethyl esters as well as its physiologically compatible salt forms. The amino-acid group R stands especially for Gly, Ala, Val, Leu, Ile, Ser, Thr, Lys, Arg, Asp, Asn, Glu, Gln, Cys, Met, Phe, Tyr, Pro, Trp, His, Orn, Thz (Thiazolidine-4-COOH). E.g. the amino-acid groups Orn, Lys, Thz are especially preferred. The abbreviations for the individual amino-acid groups are based on the trivial names of the amino acid and are known to experts in the art. The amino acids stem primarily from the L series but amino acids from the D series are also effective in the same manner. The coupling of the amino acids to the di- and tripeptide groups can be carried out in the case of the basic amino acids such as e.g. in the case of ornithine and lysine via the $\alpha$ position as well as via the terminal $\omega$ position.

DETAILED DESCRIPTION OF THE INVENTION

The long-chain alkyl chain with $(CH_2)_n$ consists of n=11–20, with n preferably=15–19 and especially n=16–17. The saturated alkyl chain is unbranched. Potential protective groups for the amino acids are e.g. tertiary butyloxycarbonyl group, carbobenzoxy group and carbobenzthio group (if necessary with p-bromine or p-nitrobenzyl group), trifluoroacetyl group, phthalyl group, o-nitrophenoxyacetyl group, trityl group, p-toluene sulfonyl group, benzyl group, benzyl groups substituted in the benzene nucleus (p-bromine group or p-nitrobenzyl group), a-phenylethyl group. Refer in this connection also to the book by Jesse P. Greenstein and Milton Winitz, Chemistry of Amino Acids, New York, 1961, John Wiley and Sons, Inc., volume 2, e.g. page 883 ff as well as The Peptides, volume 3, ed. E. Gross and J. Meienhofer, Academic Press New York, tables III and IV. These protective groups can basically also be considered for the protection of further functional side groups (OH groups, $NH_2$ groups) of the amino acids coming in question.

Hydroxy groups present (serine, threonine) are preferably protected by benzyl groups and similar groups.

The coupling of the individual amino acids to each other takes place in accordance with the methods customary for this.

The conversion of the compounds of the general formula into their acid addition salts can be carried out by causing the same to react with acids in a known manner.

Inversely, the release of the amino-acid-, di- and tripeptide compounds can be carried out by causing their acid addition salts to react with bases. Examples for such acid addition salts are hydrochloride, hydrobromide, sulfate, phosphate, fumarate, gluconate, tannate, maleate, acetate, citrate, benzoate, succinate, alginate, pamoate, malate, ascorbate, tartrate and the like. If the active substance is administered in tablet form the tablet can contain a pharmaceutically acceptable thinning agent comprising a binder such as e.g. tragacanth, corn starch or gelatine as well as contain a disintegration agent such as alginic acid and a lubricant such as magnesium stearate.

If an administration in liquid form is desired a sweetener and/or a flavoring substance can be used as part of the pharmaceutically acceptable thinning agent; in the case of intravenous administration the latter is carried out in isotonic saline, phosphate buffer solutions or the like.

The pharmaceutical compositions traditionally contain the active substance in combination with a customary, pharmaceutically acceptable carrier.

If the compounds of the general formula are used, preferably in the form of salts with acids in human medicine, a systemic administration can be carried out either by intravenous, subcutaneous or intramuscular injection or by a sublingual or nasal administration in conjunction with pharmacologically compatible carrier substances.

Drug preparations for oral administration can also be prepared. To this end the active substances are mixed with suitable known pharmaceutical thinning agents and processed in a known manner to preparations such as tablets, capsules, suspensions, emulsions, solutions or dispersible powders.

Solid preparations can be filled into capsules for oral administration. Such preparations for filling into capsules can contain the solid active material in a mixture with colloidal aluminum hydroxide, calcium hydrogen phosphate or together with an inert solid such as lactose.

Preparations in the form of tablets can be prepared in a customary manner by being coated or in the form of foaming or non-foaming preparations. To this end inert thinners or carrier substances such as magnesium carbonate or lactose can be used together with customary disintegrants such as corn starch and alginic acid and with lubricants such as magnesium stearate.

For nasal administration in the form of drops or sprays the compounds of the general formula are preferably used in a sterile, aqueous carrier which can also contain other dissolved substances such as buffers or preservatives as well as amounts of pharmacologically compatible salts or glucose sufficient to prepare an isotonic solution. The peptides of the general formula can also be administered in the form of nose powders or agents for insufflation. For these purposes the peptides are administered in finely distributed form together with a pharmacologically compatible, solid carrier substance, e.g. with finely distributed polyethyleneglycol (Carbowax® 1540), finely distributed lactose or very finely distributed silicon dioxide (Cab-O-Sil). Such remedies can also contain other additives in finely distributed form such as preservatives, buffers or surface-active agents.

The compounds of the general formula can also be administered in the form of long-acting agents with a slow release of active substance or depot effect as explained below, preferably by intramuscular injection or by implantation.

It is frequently desirable to administer the compounds of the general formula continuously or over rather long periods of time in the form of long-lasting preparations with a slow release of active substance or a depot effect. Such preparation forms can contain either a pharmacologically compatible salt of the active-substance compound with a low solubility in body liquid, e.g. salts with embonic acid, tannic acid or carboxymethyl cellulose, or the compound of the general formula in the form of a water-soluble salt together with a preventive which hinders a rapid release. In the last-named instance the compound of the general formula can be brought e.g. with non-antigenic, partially hydrolysed gelatine into the form of a viscous liquid or absorbed on a pharmacologically compatible, solid carrier substance. The active substance can also be administered in the form of a suspension in a pharmacologically compatible, liquid carrier substance. Moreover, the preparation of gels or suspensions with a non-antigenic protective hydrocolloid, e.g. sodium carboxymethyl cellulose, polyvinyl pyrrolidone, sodium alginate, gelatine, polygalacturonic acids or certain mucopolysaccharides together with aqueous or non-aqueous, pharmacologically compatible, solid carrier substances, preservatives or surface-active agents is possible. Examples of such preparations are found in customary pharmacological handbooks such as "Remington's Pharmaceutical Sciences", Mack Publishing Co., Easton, Pa., 1975. Long-acting preparations with slow release of active substance are also obtained by microencapsulation in a pharmacologically compatible coating material such as gelatine, polyvinyl alcohol or ethyl cellulose. Refer regarding further examples for coating materials and method of microencapsulation to J. A. Herbig in "Encyclopedia of Chemical Technology", vol. 13, 2d edition, Wiley, N.Y. [sic], 1967, pp. 436 to 456. Another possibility consists in preparing a few of the previously cited solid preparations, e.g. certain poorly water-soluble salts or dispersions or adsorbates of the salts, with solid carrier substances, e.g. dispersions in a neutral hydrogel of a polymerizate of ethylene glycolmethacrylate or similar cross-linked monomers (cf. U.S. Pat. No. 3,551,556) in the form of pellets which release the active substance amounts indicated above. These pellets can be implanted subcutaneously or intramuscularly. Certain compounds of the general formula which are poorly soluble in water can be prepared as suspensions in an aqueous solution or an emulsion base. Suspensions with a water base are prepared with the aid of wetting agents such as condensation products of polyethylene oxide and alkyl phenols, fatty alcohols or fatty acids and suspension agents such as hydrophilic colloids, e.g. polyvinyl pyrrolidone. Suspensions with an emulsion base are prepared by suspending the peptide with the aid of a wetting agent and suspension agents in the emulsion base, using the emulsifiers explained above. Suspensions can additionally contain buffers and/or sweeteners, aromatic substances, colorants, preservatives and antioxidants.

For parenteral administration the use of a water-soluble salt of the general formula in aqueous, sterile solution is preferred. Examples of preservatives are p-hydroxybenzoic-acid methyl- and propyl esters, which are added together with other soluble components like amounts of sodium chloride or glucose sufficient for preparing isotonic solution. Peptides of the general formula which are poorly soluble in water can also be administered intramuscularly in the form of solutions or suspensions in sterile, liquid, non-aqueous carriers, e.g. in vegetable or animal oils. The previously named, additional solution components or suspension agents can be contained, if necessary, in this instance.

The effectiveness of the compounds defined in accordance with the invention was tested as to their in vitro cytotoxicity. The investigations about inhibition of colony formation in soft agar (colony assay) were carried out in conformity with the method of Hamburger and Salmon (A. W. Hamburger, S. E. Salmon, "Primary Bioassay of Human Myeloma Stem Cells", J. Clin. Invest. 60: 846–854 (1977); A. W. Hamburger and S. E. Salmon, "Primary Bioassay of Human Tumor Stem Cells", Science 197: 461–463 (1977)). The tumor cells were incubated in RPMI-1640 medium with 20% fetal calf serum and 0.3% agar in the presence of different concentrations of the test substance at 37° C., 95% relative air humidity and 5% $CO_2$. Triple values were taken in each instance. The incubation time was 6 days for L1210 mouse leucemia and 8 days for KB human mucous-membrane carcinoma. The colonies formed (>50 cells) were subsequently counted.

The concentration of the test substance, which resulted in an inhibition of colony formation of 90% ($EC_{90}$), was determined by graph.

The results of the in vitro investigations of a few compounds are shown in the following table. The compounds with the highest activity against KB cells are D-20 994, D-20 995 and D-22 267, against L 1210 cells D-21 979 and D-22 628.

| Substance | Description | Cytotoxicity in vitro $EC_{90}$ | |
|---|---|---|---|
| | | L 1210 µg/ml | KB µg/ml |
| D-20 989 | H—ORN(ORN)—$NHC_{18}H_{37}$.3HCL | 3.1 | 1.3 |
| D-20 990 | H—ORN[(ORN)ORN]—$NHC_{18}H_{37}$ 4HCl | >10 | 1.7 |
| D-20 994 | H—LYS(LYS)—$NHC_{18}H_{37}$.3HBr | 3.2 | 0.8 |
| D-20 995 | H—LYS[(LYS)LYS]—$NHC_{18}h_{37}$.4HBr | >3 | 0.9 |
| D-21 621 | H—LYS(LYS)—$NHC_{18}H_{37}$.3HCl | 2.2 | 1.4 |
| D-21 979 | H—THZ—$NHC_{14}H_{29}$ | 0.3 | 3.1 |
| D-21 980 | H—THZ—$NHC_{16}H_{33}$ | 3.4 | 3.1 |
| D-22 267 | H—LYS—LYS—$NHC_{18}H_{37}$ | 3.1 | 0.3 |
| D-22 628 | H—D—LYS(D—LYS)—$NHC_{18}H_{37}$.3HCL | 0.8 | 1.1 |

The short designations of the compounds furnish an indication about the coupling of the di- and tripeptide compounds. Thus, e.g. H-LYS-LYS-NH-R signifies that an α coupling is present between the amino acids whereas H-LYS(LYS)-NH-R signifies a terminal ω coupling of the amino acids. The amino-acid-, dipeptide- and tripeptide formulas with chirality data are always the L forms whereas the D forms are characterized separately as such.

The compound H-LYS(LYS)-$NHC_{18}H_{37}$.3HCL (D-21621) was tested separately on human tumors transplanted into the naked mouse. A tumor inhibition of 37% of the control was achieved for the small-cell bronchial carcinoma LXFS 538 with a dose of 45 mg/kg, administered i.p. per day 1.5 and 9. The compound achieved a tumor inhibition of 46% of the control for ovarian carcinoma OVXF 899 under the same conditions. This tumor is resistant to all standard cytostatic agents.

The compounds of the general formula are synthesized in accordance with known methods such as e.g. by the classic solution couplings. The normal progression is that the long-chain alkylamine is caused to react with the protected amino acid and subsequently the protective groups are removed in a known manner. Classic solution synthesis is described in detail in the treatise "Methoden der Organischen Chemie (Houben-Weyl). Volume 15/1;15/2 Synthese von Peptiden" [German—Methods of Organic Chemistry (Houben-Weyl), Synthesis of Peptides], E. Wunsch (editor) (1974), Georg Thieme Verlag, Stuttgart, Federal Republic of Germany.

Among the classes of α-amino protective groups e.g. fluorenylmethoxycarbonyl (Fmoc) or t-butoxycarbonyl (BOC) can be cited. A protective group for the hydroxyl group of the serine can be e.g. benzyl (Bzl) and 2,6-dichlorobenzyl (DCB). Benzyloxycarbonyl (Z) and 2-chlorobenzyloxycarbonyl]Z-(2-Cl)] are exemplary for attached side-chain amino protective groups of Lys or Orn.

Activated esters of benzyloxycarbonyl amino acids such as e.g. N-hydroxysuccinimide ester or 2,4,5-trichlorophenyl ester and 4-nitrophenyl ester are especially well suited for the incremental [progressive] condensation of amino acids. The aminolysis of the two latter active esters can be catalyzed very well by N-hydroxy compounds exhibiting approximately the acidity of acetic acid such as e.g. 1-hydroxybenzotriazol. Groups which can be hydrogenated off such as e.g. the benzyloxycarbonyl group (=Z group) or groups which can be split off in a slightly acidic manner such as e.g. the 2-(p-diphenyl isopropyloxycarbonyl- or 2-(3,5-dimethoxyphenyl)-isopropyloxycarbonyl group present themselves as intermediary amino protective groups.

The incremental condensation takes place by means of synthesis from the corresponding amino acids, which are optionally protected in a customary manner, in a traditional manner.

EXAMPLES

The preparation of
H-Orn-$NHC_{16}H_{33}$.2HBR
H-Orn-$HNC_{18}H_{37}$.2HBr
H-Orn-Orn-$HNC_{18}H_{37}$.3HCl
H-Orn(Orn)-$HNC_{18}H_{37}$.3HCl is described by G. Kellner and M. Lieflãnder in Z. Naturforsch., B, Chem. Sci, 46 (8) 1098–1104 (1991). The novel compounds can also be prepared according to the formula contained therein. The following preparation formula is indicated by way of example for the derivatives H-LYS[(LYS)LYS]-$NHC_{18}H_{37}$.4HBr and H-D-LYS(D-LYS) $NHC_{18}H_{37}$.3HCl:

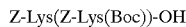
Z-Lys(Z-Lys(Boc))-OH

Amounts added:
Z-Lys(Boc)-OSu 7.16 g (15.0 mmoles)
Z-Lys-OH 4.63 g (16.5 mmoles)
Triethylamine 2.5 ml (18.0 mmoles)
Execution: The succinimidester is dissolved in 50 ml dioxane. The amine component dissolved in 50 ml is added thereto with the base at room temperature. After 20 h the reaction mixture is worked up in accordance with the following general instruction.

1 mmole of the N-protected amino-acid- or peptide succinimidester is dissolved in 3–6 ml dioxane, depending on the solubility. A mixture of 1.2 mmoles triethylamine and 1.1 mmoles amino component is added in each instance all at once into 3–6 ml water (the amount of water should correspond to the volume of dioxane) at room temperature under vigorous agitation. After 24 h reaction time the mixture is acidified with 0.5M solution of citric acid, 2.5 ml acid per mmole succinimidester, and immediately extracted several times with ethyl acetate (EE). The amount of EE required rises considerably with the peptide length. The combined organic phases are washed three times with water and dried over $Na_2SO_4$. It is often not advantageous to draw the solvent completely off since the oily product can then not be brought to crystallization even with the aid of precipitating agents. As a rule, diisopropyl ether, hexane, diethyl ether or petroleum ether serve as precipitating agents. In individual instances a precipitation as DCHA salt is more advantageous.

Usually, the first crystals accumulate when the EE is drawn off already; the crystallization is completed at 4° C. under the addition of a little diisopropyl ether.
Raw yield: 9.45 g (14.7 mmoles, 98%)
Melting point: 138°–139° C.
Recrystallization from EE
Pure yield: 9.0 g (14 mmoles, 93%)
Melting point: 140°–141° C.

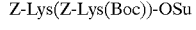
Z-Lys(Z-Lys(Boc))-OSu

Amounts added:
Z-Lys(Z-Lys(Boc))-OH 7.71 g (12.0 mmoles)
N-hydroxysuccinimidester 1.38 g (12.0 mmoles)
DCC 2.46 g (12.0 mmoles)
Execution: According to the following general formula
1 mmole N-protected amino-acid- or peptide derivative and 1 mmole N-hydroxysuccinimide are each dissolved in 5 ml THF and cooled to −10° C. 1 mmole DCC is then added to each and the mixtures agitated 1.5 h at −10° C. and 24 h at room temperature. The precipitated, finely crystalline N,N'-dicyclohexyl urea is filtered off and washed with EE.

The filtrate is evaporated to low bulk and the accumulating oil brought to crystallization either by triturating with petroleum ether or by precipitation from EE/diisopropyl ether. The recrystallization takes place from suitable solvents. In the case of batches with educt amounts above 12 mmoles byproducts which are very difficult to remove can form in a more intense fashion.

The splendid solubility of the peptide in THF stands out.
Raw yield: 8.6 g (11.6 mmoles, 97%)
Melting point: 127°–129° C.
Recrystallization from ethanol
Pure yield: 8.1 g (10.9 mmoles, 91%)
Melting point: 130°–132° C.

Boc-Lys(Z-Lys(Z-Lys(Boc))-OH

Amounts added:
Z-Lys(Z-Lys(Boc))-OSu 7.40 g (10.0 mmoles)
Boc-Lys-OH 2.71 g (11.0 mmoles)
Triethylamine 1.70 ml (12.0 mmoles)
Execution: The succinimidester is dissolved in 50 ml dioxane. The amine component dissolved in 50 ml H$_2$O and NEt$_3$ are added at room temperature and agitated 24 h. After acidifying with citric acid and three extractions with EE the combined organic phases are washed several times with H$_2$O and dried over Na$_2$SO$_4$. The solution is evaporated to a low bulk of a few ml. The first crystals form thereby on the flask edge. These crystals are brought by agitation into the residue, whereupon the crystallization begins very rapidly. EE is added several times in order to prevent clumping. The crystallization is completed at 4° C.
Raw yield: 8.54 g (9.8 mmoles, 98%)
Melting point: 153°–154° C.
Recrystallization takes place from methanol/EE/diisopropyl ether
Pure yield: 8.19 g (9.4 mmoles, 94%)
Melting point: 154°–155° C.

Boc-Lys(Z-Lys(Z-Lys(Boc))-OSu

Amounts added
Boc-Lys(Z-Lys(Z-Lys(Boc))-OH 6.97 g (8.0 mmoles)
N-hydroxysuccinimide 0.92 g (8.0 mmoles)
DCC 1.64 g (8.0 mmoles)
Execution: The peptide dissolves very poorly in THF, so that 80 ml THF and sonication in an ultrasonic bath are necessary for the dissolving process. The matter is cooled to −10° C. and the SuOH dissolved in 10 ml THF and the DCC dissolved in 30 ml THF are added separately. After 1 h agitation at −10° C. and 20 h at room temperature the reaction mixture is quite concentrated. The pulp is taken up in methanol and the partially non-dissolved dicyclohexyl urea is filtered off. During the evaporation to low bulk of the mixture precipitated urea must be removed three times more. The crystallization of the product is achieved by the addition of diisopropyl ether.
Raw yield: 7.74 g (8.0 mmoles, 100%)
Melting point: 119°–120° C.
Recrystallization takes place from ethanol
Pure yield: 7.17 g (7.4 mmoles, 93%)
Melting point: 120°–121° C.

Boc-Lys(Z-Lys(Z-Lys(Boc)))-NHC$_{18}$H$_{37}$

Amounts added:
Boc-Lys(L-Lys(Z-Lys(Boc)))-OSu 4.84 g (5.0 mmoles)
Octadecylamine 1.35 g (5.0 mmoles)
Execution: The succinimidester is dissolved in 50 ml dioxane and added to a solution of the amine in 30 ml CHCl$_3$. The batch gels after 11 h. A solution is obtained again by means of the addition of CHCl$_3$ and heating to 40° C. The solvent is removed and the residue brought to crystallization with diisopropyl ether.
Pure yield: 4.61 g (4.1 mmoles, 82%)
Melting point: 139°–142° C.

H-Lys(H-Lys(H-Lys))-NHC$_{18}$H$_{37}$ · 4HBr

Amounts added:
Boc-Lys(Z-Lys(Z-Lys(Boc)))-NHC$_{18}$H$_{37}$ · 2.24g (2.0 mmoles)
HBr/glacial acetic acid 15.8 ml
Cold 33% HBr/glacial acetic acid is poured over the compound at 4° C. and the mixture agitated 2–3 h at 10° C. under the exclusion of moisture. The hydrobromide precipitates almost totally, usually during the reaction already. After the addition of diethyl ether (DE) the product is removed by suction and washed well with DE. The raw product still has a heavy odor of benzylbromide and is immediately recrystallized several times. If the product is soluble in the acetic acid—diethyl ether mixture the solvent is drawn off on a water-jet vacuum and the residue taken up in a little ethanol. The product can be precipitated by the addition of DE or EE. It is purified by recrystallization from methanol/EE.
Pure yield: 1.52 g (1.6 mmoles, 78%)
Melting point: sintered above 226° C.

H-D-Lys(D-Lys)-NH-C$_{18}$H$_{37}$3HCl

Boc-D-Lys-OH is reacted with equimolar amounts [or "in equimolar amounts"—grammatical error in text] of triethylamine and Boc-D-Lys(Boc, Osu in DMF to the protected dipeptide Boc-D-Lys(Boc-D-Lys(Boc))-OH. The latter is coupled with DPPA and a 10% excess octadecylamine in THF to the Boc-D-Lys(Boc-D-Lys(Boc))-NH-C$_{18}$H$_{37}$. The product, purified by column chromatography over silica gel is crystallized out of THF/diisopropyl ether. Flash point [melting point]: 70°–71° C. After splitting off of the protective groups with TFA the trihydrochloride of the dipeptide amide is precipitated with HCl in ether from ethanol and then recrystallized from ethanol. Flash point: 215° C. (decomposition)

We claim:

1. A long-chain, unbranched alkylamide of the formula

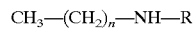

in which n=11–20 and R is a di- or tripeptide of amino acids selected from the group consisting of lysine, serine, proline, thiaproline, and hydroxyproline and their D- and L-enantiomers as well as their physiologically compatible salt forms, wherein lysine can be coupled via the α position as well as via the terminal ω position.

2. The long-chain alkylamide according to claim 1 in which n=15–19, and R contains a lysine, serine or proline.

3. The long-chain alkylamide according to claim 1 in which n=17.

4. The alkylamide according to claim 1 which is H-Lys-Lys-NH-(CH$_2$)$_{17}$-CH$_3$.3HX in which X=Cl or Br.

5. The alkylamide according to claim 1 which is H-Lys(Lys)-NH-(CH$_2$)$_{17}$-CH$_3$.3HX in which X=Cl or Br.

6. The alkylamide according to claim 1 which is H-D-Lys(D-Lys)-NH-(CH$_2$)$_{17}$-CH$_3$.3HX in which X=Cl or Br.

7. A pharmaceutical preparation containing at least one alkylamide of the formula

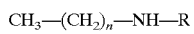

in which n=11–20 and R is a di- or tripeptide of amino acids selected from the group consisting of lysine, serine, proline, thiaproline, hydroxyproline and ornithine and their D- and L-enantiomers as well as their physiologically compatible salt forms, and wherein lysine and ornithine can be coupled via the α position as well as via the terminal ω position, and pharmaceutical auxiliary substances and carrier substances.

8. A method for the treatment of tumors, bronchial asthma, hay fever, allergic rhinitis and muscular rheumatism, said method comprising administering a therapeutically effective amount of an alkylamide of the formula

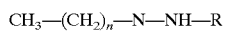

in which n=11–20 and R is a di- or tripeptide of amino acids selected from the group consisting of lysine, serine, proline, thiaproline, hydroxyproline and ornithine and their D- and L-enantiomers as well as their physiologically compatible salt forms, and wherein lysine and ornithine can be coupled via the α position as well as via the terminal ω position, to an individual in need of such treatment.

* * * * *